United States Patent [19]

Ton

[11] Patent Number: 4,671,768
[45] Date of Patent: Jun. 9, 1987

[54] IMPLANT AS WELL AS A DENTAL PROSTHESIS ATTACHED TO ONE OR MORE OF SUCH IMPLANTS

[76] Inventor: Michael A. Ton, Badhuisstraat 45, 4381 LN, Vlissingen, Netherlands

[21] Appl. No.: 641,961

[22] PCT Filed: Dec. 5, 1983

[86] PCT No.: PCT/NL83/00048
  § 371 Date: Aug. 6, 1984
  § 102(e) Date: Aug. 6, 1984

[87] PCT Pub. No.: WO84/02264
  PCT Pub. Date: Jun. 21, 1984

[30] Foreign Application Priority Data
  Dec. 6, 1982 [NL] Netherlands .......................... 8204714

[51] Int. Cl.⁴ ............................................... A61C 8/00
[52] U.S. Cl. ...................................... 433/174; 433/80; 433/173; 433/201.1
[58] Field of Search ............... 433/173, 174, 175, 201, 433/80, 81, 224, 221

[56] References Cited

U.S. PATENT DOCUMENTS

| 237,043 | 1/1881 | Palmer | 433/221 |
| 2,210,424 | 8/1940 | Morrison | 433/175 |
| 2,347,567 | 4/1944 | Kresse | 433/174 |
| 2,857,670 | 10/1958 | Kiernan | 433/173 |
| 4,186,486 | 2/1982 | Gordon | 433/201 |

FOREIGN PATENT DOCUMENTS

| 2040781 | 1/1971 | France | 433/174 |
| 198909 | 10/1965 | Sweden | 433/173 |
| 17530 | 7/1896 | United Kingdom | 433/221 |

Primary Examiner—John J. Wilson

[57] ABSTRACT

Implant (1) comprising an anchoring part having one or more fixing means (2) as well as a prosthesis part adapted to fix a dental prosthesis, which implant is provided with a cavity (4) extending from the prosthesis part into the anchoring part, the wall of the anchoring part is perforated at one or more spots (5) and the prosthesis part is provided with a removable closing means (3) for the cavity; when the implant is implanted the cavity of the implant may contain a medicine for protecting the implant against pathogenic bacteria etc.

5 Claims, 2 Drawing Figures

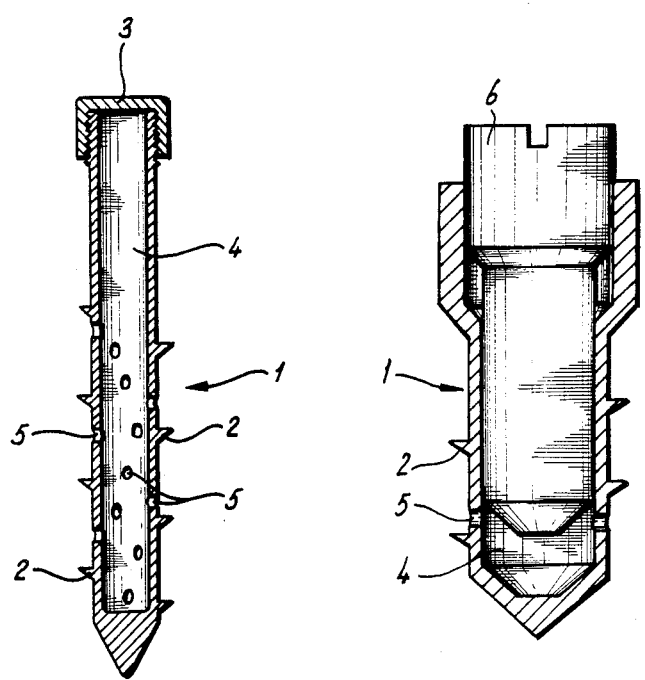

_4,671,768_

IMPLANT AS WELL AS A DENTAL PROSTHESIS ATTACHED TO ONE OR MORE OF SUCH IMPLANTS

BACKGROUND OF THE INVENTION

The invention relates to an implant comprising on the one hand an anchoring part having one or more fixing means for anchoring the implant to the bone and on the other hand a prosthesis part adapted to fix a dental prosthesis to the implant.

SUMMARY OF THE INVENTION

The known and nowadays most applied implants have a metal anchoring part and the form of a plate, needle or screw. With these implants the anchoring is based on the mechanical engagement of the implanted body and the bone by forming of a tissue covering at the interface of the bone and the implanted body.

Further, from Dutch patent application No. 66,03182 implants of ceramic material like metal oxides especially aluminum oxide, -silicates, -carbides, -borides, -nitrides, -silicides or glass are known. These implants having e.g. the shape of pens are placed in hollow roots.

However, after the implantation of the known implants whereby the implant is partly in the body ("milieu interieur") and partly outside the body ("milieu exterieur"), as a rule infections appear because the transition region of "milieu interieur" to "milieu exterieur" is a "porte d'entrée" for pathogenic bacteria and other pathogenic germs. At this "porte d'entrée" the bacteria etc. coming out of the oral cavity which in view of the temperature and humidity present therein is an ideal breeding place for a.o. bacteria, penetrate into the body against the plasma stream. The body reacts thereon by starting a defensive reaction inducing the forming of pus. Because of these defensive reactions and the complications belonging thereto normally the placed implant gets lost or should even be removed for stopping a steady expanding infection.

The invention is aimed at the removal of the abovementioned objection so that the chances of survival of an implanted implant can be improved substantially.

It was found that the above described disadvantage of the known implants can be removed by providing the implant of a hollow cavity which extends from the prosthesis part into the anchoring part, the wall of the anchoring part is perforated at one or more spots and the prosthesis part is provided with a removable closing means for the cavity. More in particular, in this cavity a medicine like an antibiotic can be placed which by diffusion/osmosis via the perforations present in the wall of the anchoring part will leave the cavity of the implant and will be carried away with the plasma stream in the direction of the "milieu interieur/milieu exterieur". Therefore a considerable concentration of antibiotic is present at the transition region of "milieu interieur/milieu exterieur" so that this "porte d'entrée" for bacteria etc. is closed. Normally an antibiotic having a broad spectrum like gentamycin is used.

Apart from the abovementioned advantage the implants according to the invention have the possibility to make instantaneous views of the condition of the implanted implant at any time. By removing the removable closing means one may carry out a puncture in the implant after which by means of a laboratory test it can be determined which bacteria/cells are present in the implant. In case of the presence of undesired bacteria/cells in the implant it is possible to combat these undesired bacteria/cells by means of a specific medicine. Therefore with the implants according to the invention it is possible to check constantly the condition of the implant and if desired to influence it. Further, it is possible to replenish or to replace the antibiotic present in the implant after some time e.g. at the half yearly check so that an optimum protection of the implant is guaranteed.

The implant according to the invention is preferably made of metal, e.g. dental gold having the composition of 65-85% gold, 1-4% palladium, 1-10% platinum, 10-15% silver, 0-10% copper and 0-1% zinc. As marketed dental gold metals are mentioned: "Degudent-G" (98% noble metal alloy) and "Permador". Next to the above alloys also noble metal alloys are qualified. Except noble metal alloys also other inert alloys having a good resistance against corrosion as well as against strong mechanical loads can be used e.g. alloys on the basis of cobalt, chromium, titanium and molybdenum respectively on the basis of chromium, cobalt and nickel.

The fixing means of the anchoring part of the implant is preferably a screw thread of the retinating type having a great speed which speed resembles the one of a marrow screw.

The removable closing means for the cavity of the implant is preferably a screw cap which can be screwed on the free end of the prosthesis part of the implant. However, also other closing means can be used which depend on the prosthesis later to be used on behalf of the rehabilitation of the set of teeth which are under treatment.

The diameter of the perforations in the wall of the anchoring part of the implant according to the invention should have such a size that a sufficient passage of body fluids may take place. However, the diameter respectively the number of perforations are limited by the fact that the structural strength of the implant should be considerable in view of the forces which can be expected during the implantation of the implant in the bone. So an univocal indication of the diameter respectively number of perforations cannot be given and is also dependent on the material of the implant in question.

DETAILED DESCRIPTION OF THE INVENTION

The invention will best be understood by the following more detailed description thereof in relation to the accompanying drawings wherein:

FIG. 1 is an elevational view in section of an implant according to the invention; and FIG. 2 is an elevational view, partly in section of a modified form of said implant showing an obturator contained therein.

An embodiment of the implant according to the invention is illustrated in longitudinal section in the enclosed FIG. 1 in which the implant of the screw pin type (1) made of dental gold comprises a cavity (4) which extends from the prothesis part into the anchoring part. The anchoring part has been provided with a screw thread (2) of the retinating type having a great speed which resembles the one of a marrow screw. The wall of the hollow implant has a thickness of at least 0.4 mm. Further the wall of the anchoring part is provided with one or more perforations (5) having a diameter of 0.5-1 mm. The free end of the prosthesis part of the implant is supplied with a screw thread for closing the cavity by means of a screw cap (3).

Further the invention relates to a dental prosthesis like an artificial tooth, bridge or a complete upper respectively lower set of artificial teeth which is attached to one or more of the implants according to the invention and the cavity of the concerning implant respectively implants mounted in the bone is supplied with an antibiotic. From the experiences gained up to now it has appeared that such dental prosthesis on the basis of the implants according to the invention do have an optimum lifetime.

When in the post implant period it is definitely evident the implant is settled and there is no more need for a local antibiotic, the cavity inside the implant may be occluded by an obturator (closing the perforations) which is screwed in (clockwise) (vide FIG. 2 illustrating among others an embodiment of the obturator having number (6), whereas the numbers (1), (2), (4) and (5) have the meanings mentioned above).

Once the need arises to utilise a local antibiotic again, the obturator may easily be extracted from the cavity by screwing the obturator out (counter clockwise). The cavity is again ready to receive an antibiotic filling and is for instance closed by screwing a screw cap on the top of the implant.

I claim:

1. A dental implant comprising a hollow cylindrical metallic body having a central cavity, an anchoring portion, and a prosthesis portion adapted for fixing thereto a dental prosthesis, said anchoring portion being provided on the outer wall thereof with a screw thread for securing said implant to bone tissue and with perforations connecting said central cavity through said outer wall to administer medication to said bone tissue, said prothesis portion being provided with removable closing means to close said central cavity.

2. An implant according to claim 1, wherein the material of which it is constructed is selected from the group consisting of dental gold alloys, noble metal alloys, and other alloys having good resistance to corrosion and strong mechanical loads.

3. An implant according to claim 1, wherein said removable closing means is a screw cap which is screwed on to the free end of the prosthesis portion.

4. A dental implant comprising a hollow cylindrical metallic body having a central cavity, an anchoring portion, and a prosthesis portion adapted for fixing thereto a dental prosthesis, said anchoring portion being provided on the outer wall thereof with a screw thread for securing said implant to bone tissue and with perforations connecting said central cavity through said outer wall to administer medication to said bone tissue, said prothesis portion being provided with removable closing means to close said central cavity, wherein the implant is made of a material selected from the group consisting of dental gold and a titanium alloy, and wherein the central cavity in the implant has a diameter of from about 2-2.5 mm, the wall of the implant has a thickness of at least about 0.4 mm and the perforations in the wall have a diameter of from about 0.5-1 mm.

5. An implant according to any one of claims 2, 3 or 4 wherein said central cavity contains a medicinal agent.

* * * * *